United States Patent [19]
Nishi et al.

[11] Patent Number: 6,012,169
[45] Date of Patent: Jan. 11, 2000

[54] GLOVE MADE OF POLYVINYL CHLORIDE RESIN

[75] Inventors: Yasutaka Nishi, Takasago; Akio Miyake, Himeji, both of Japan

[73] Assignee: Showa Kabushiki Kaisha, Hyogo-ken, Japan

[21] Appl. No.: 09/248,097

[22] Filed: Feb. 11, 1999

[30] Foreign Application Priority Data

Feb. 17, 1998 [JP] Japan ................................. 10-034920

[51] Int. Cl.[7] ............................................. A41D 19/00
[52] U.S. Cl. ................................................. 2/161.7; 2/167
[58] Field of Search .............................. 2/16, 159, 161.7, 2/167; 427/2.3; D29/113

[56] References Cited

U.S. PATENT DOCUMENTS

| | | | |
|---|---|---|---|
| 4,853,978 | 8/1989 | Stockum | 2/167 |
| 5,003,638 | 4/1991 | Miyake et al. | |
| 5,019,096 | 5/1991 | Fox, Jr. et al. | 623/1 |
| 5,069,907 | 12/1991 | Mixon et al. | |
| 5,725,867 | 3/1998 | Mixon | 424/402 |
| 5,772,640 | 6/1998 | Modak et al. | 604/265 |

FOREIGN PATENT DOCUMENTS

WO 98/30094  7/1998  WIPO.

*Primary Examiner*—Diana Oleksa
*Assistant Examiner*—Katherine Moran
*Attorney, Agent, or Firm*—James Creighton Wray; Meera P. Narasimhan

[57] ABSTRACT

An object of the invention is to provide a polyvinyl chloride resin-made glove exhibiting an antimicrobial activity both on inner and outer surfaces of the glove which has a simple constitution and is easily fabricated to be cost-competitive. The glove is constituted of a base layer 1 formed of the polyvinyl chloride resin and an antimicrobial agent including layer 2 of which major composition is a polyacrylic resin formed on one of the surfaces of the base layer, no matter what the surface may be the outer one or the inner one of the glove. A base layer thickness of the glove is reduced less than a specified thickness through which the antimicrobial agent can penetrate diffusibly from one of surfaces to the opposite surface of the glove.

2 Claims, 1 Drawing Sheet

GLOVE MADE OF POLYVINYL CHLORIDE RESIN

BACKGROUND OF THE INVENTION

1. Field of the Invention

The present invention relates to a glove made of polyvinyl chloride resin of which inner and outer surfaces are both provided with an antimicrobial activity. 2. Brief Description of the Prior Art As a conventional example of gloves made of a polyvinyl chloride resin film furnished with the antimicrobial activity, a Japanese Utility Model (U) of the Laid-open Number: 07-31819 (1995) discloses a glove having a dually layered structure fabricated by coating an inner surface of a base layer acting as a main layer of the glove with a surfactant which is co-polymerized antimicrobial compositions formed of alkyl esters either of acrylic acid or of tertiary ammonium methacrylic acid to provide an antimicrobial film, thereby to prevent the inner surface of the glove from contamination generated by bacteria as well as from breeding the bacteria.

Beside this, a Japanese Patent Application (A1) of the Laid-open Number: 03-199403 (1991) discloses another glove having a triply layered structure manufactured by supplying both the inner and the outer surfaces of the base layer of the glove with highly polymerized organic layers (polyethylene films) which include antimicrobial active zeolite for acting as antimicrobial active films, thereby to prevent both the inner and the outer surfaces of the glove from contamination induced by the bacteria and from breeding the bacteria.

As the former conventional glove is provided inside the base layer of the glove with the antimicrobial film obtained by polymerization of the antimicrobial composition as mentioned above, the glove is incapable of preventing the outer surface of the glove from the bacteria-induced contamination and from breeding the bacteria due to a lack in antimicrobial activity on the outer surface because the antimicrobial agent does not diffusibly transfer to the outer surface of the glove.

On the other hand, the latter conventional glove having the triply layered structure intended to prevent both the inner and the outer surfaces from the bacteria-induced contamination and from breeding the bacteria has encountered problems that not only manufacturing steps turn complicated but also manufacturing costs turn expensive which results in an unrealistic application.

SUMMARY OF THE INVENTION

The present invention is carried out to solve the so far problems mentioned above. An object of the invention is to reduce a base layer thickness of a glove less than, for instance, 0.2 millimeters (referred to as "mm" hereinafter) that can guarantee a diffusibly transferring of an antimicrobial agent so that an antimicrobial activity is given even on a surface which is unprovided with an antimicrobial agent including layer and located on an opposite side of the base layer with respect to another surface directly contacted with the antimicrobial agent including layer, so long as the antimicrobial agent including layer is formed merely on one of the surfaces, no matter what the surface may be the inner one or the outer one of the base layer of the glove, thereby to provide a sanitary glove which can prevent both the outer and the inner surfaces from a contamination induced by adhering bacteria as well as from breeding the bacteria.

The problems mentioned above are solved by constitutions according to the present invention as follows:

(1) A glove comprising:

a base layer formed of a polyvinyl chloride resin; and an antimicrobial agent including layer of which major composition is a polyacrylic resin for including an antimicrobial agent, wherein:

aforesaid antimicrobial agent including layer is provided either on a front surface or on a rear surface of aforesaid base layer; and a base layer thickness of the glove is reduced less than a specified thickness wherethrough the antimicrobial agent can diffusibly transfer from the surface provided with the antimicrobial agent including layer to the opposite surface ungiven with the antimicrobial agent including layer.

(2) The glove according to the constitution described in (1), wherein:

the base layer thickness of the glove is reduced less than 0.2 mm.

(3) The glove according to the constitution described in (1), wherein:

the antimicrobial agent included in the antimicrobial agent including layer is either a synthetic zeolite or a natural zeolite which contains at least one of metallic ions consisting of silver, copper and zinc.

In the constitutions according to the present invention mentioned above, as the base layer thickness of the glove is reduced to be as thin as and preferably less than 0.2 mm, the antimicrobial agent which is provided either on the internal surface or on the external surface diffusibly moves into the base layer and penetrates the layer to bring about the antimicrobial effect even on the opposite surface that the antimicrobial agent is unprovided. Although this phenomenon has not been scientifically verified yet, the antimicrobial agent presumably partially co-diffuses with plasticizers such as di-2-ethylhexyl phthalate (referred to as "DOP") etc., which are included in the polyvinyl chloride resin, into the polyvinyl chloride resin within a limit in length of 0.2 mm to penetrate to the opposite surface to exhibit the antimicrobial effect. Accordingly, the danger that either the external or the internal surface of the glove is contaminated with the bacteria and breeds the bacteria turns preventable.

DETAILED DESCRIPTION OF THE PREFERRED EMBODIMENTS

Hereinafter described are the preferred embodiments according to the present invention with reference to the drawings of FIGS. 1 and 2. The best modes contemplated by the inventors during carrying out the invention into practice will also be described corresponding to the preferred embodiments.

EMBODIMENT 1

Figure 1:
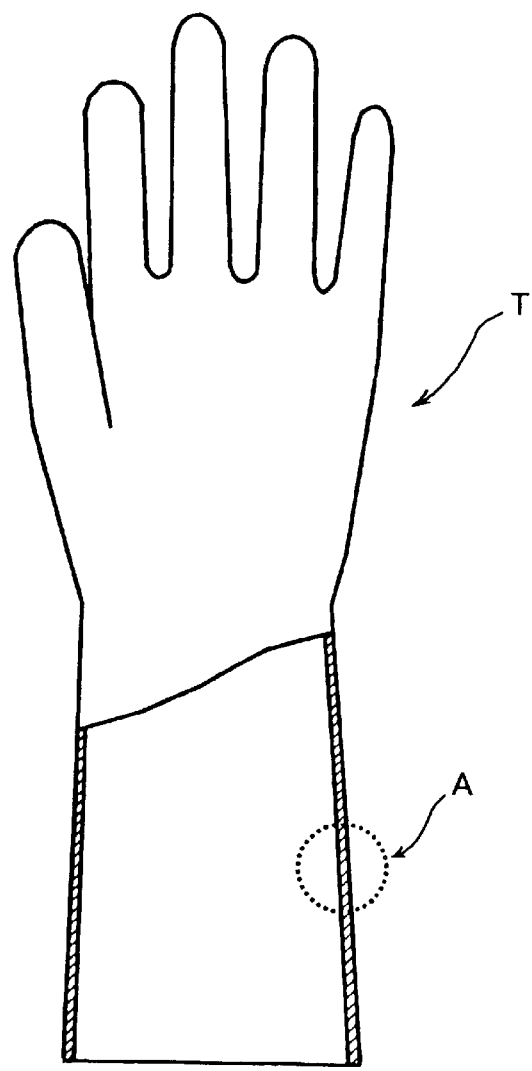
FIG. 1 is a partly longitudinally cross-sectioned front view showing embodiments of polyvinyl chloride resin-made gloves according to the present invention.

FIG. 1 is a partly longitudinally cross-sectioned view of an antimicrobial active polyvinyl chloride resin-made glove T of embodiments according to the present invention. FIG. 2 is an enlarged view of a portion enclosed by a circle A in FIG. 1.

Figure 2:
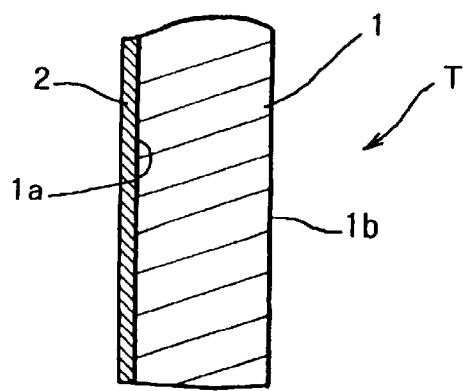
FIG. 2 is an enlarged view of a portion enclosed by a circle "A" in FIG. 1.

In FIG. 2, a numeric sign 1 stands for a basic layer having 0.1 mm in thickness which maintains an outer surface 1a having an antimicrobial activity while 2 stands for an antimicrobial agent including layer having five micrometers in thickness formed of a co-polymerized methacrylic acid ester which includes a silver-descendent zeolite as the antimicrobial agent. In the present embodiment, aforesaid antimicrobial agent including layer 2 is provided on an internal surface 1b of the base layer 1 of the glove. The base layer thickness of the glove is as thin as 0.1 mm so that the antimicrobial agent diffusibly moves into the basic layer 1 penetrating through the layer 1 to reach the external surface 1a, wherein it can provide the antimicrobial activity even on the outer surface 1a of the glove as mentioned above.

An exemplified manufacturing step of the glove T according to the present invention is to be described step by step as follows:

(STEP 1) First, a glove manufacturing mold for manufacturing a glove which is formed of pottery to be hand print-shaped (referred to as "mold" hereinafter) is warmed-up to be about 70 degree Celsius (referred to as "°C" hereinafter). Next, the mold is immersed into a polyvinyl chloride paste which does not include any antimicrobial agent. Compositions of the paste are tabulated on Table 1. After pulling up out of the paste, the mold is subjected to a semi-curing step at 250° C. for 60 seconds to fabricate a 0.1 mm-thick base layer 1 of the glove and then cooled.

TABLE 1

| COMPOSITION | PARTS BY WEIGHT |
|---|---|
| Polyvinyl Chloride Resin (Degree of Polymerization = 1,500) | 100 |
| Plastilizer (DOP) | 90 |
| Co-stabilizer (ESBO) | 3 |
| Stabilizer (Ca—Zn) | 3 |
| Thickener ($SiO_2$) | 0.2 |

"ESBO" on the table herein represents epoxidized soybean ail.

(STEP 2) The mold that the base layer 1 of the glove is fabricated on the surface is further immersed into an emulsion formed of co-polymerized resin composed of a methacrylic acid ester including an antimicrobial agent of 0.83 at a weight % with respect to a mixture. Compositions of the mixture are shown on TABLE 2. After pulling out from the emulsion, the mold is subjected to a heat treatment at 200° C. for 10 minutes to form the five micrometers-thick antimicrobial agent including layer 2.

TABLE 2

| COMPOSITION | PARTS BY WEIGHT |
|---|---|
| Methyl Methacrylate Co-polymerized Resin | 3.327 |
| Surfactant | 0.160 |
| Thickner | 0.400 |
| Antiseptic Agent | 0.080 |
| Antimicrobial Agent (Ag-Zeolite) | 0.033 |
| Water | 96.000 |

(STEP 3) When the antimicrobial agent including layer 2 is cooled, removing the base layer 1 out of the mold by inverting inside out provides the glove T according to the embodiment.

An antimicrobial activity test is performed utilizing a dropping adhesion method with respect to the glove T which is obtained by the manufacturing steps mentioned above. The obtained test results a retabulated on TABLE 3.

In the test, a mycelial solution including either colon bacillus (*Escherichia coli*) or *Staphylococcus aureus* is first dripped onto either the inner surface or the outer surface of a test piece to be tested which is cut out from the glove. Prior to an incubation test, numbers of viable cells located on the test piece are counted next. The test piece is then stored being contacted with a film which is newly disposed overlying the mycelial including solution. After a period of 24 hours elapses, the viable cell counts in the mycelial including solution are confirmed again. Herein so called Mueller Hinton 2 is used as culture media of the incubation test.

COMPARATIVE EMBODIMENT

A comparative embodiment which is quite the same as EMBODIMENT 1 except for the base layer thickness of the glove is manufactured to be compared with EMBODIMENT 1 concerning the antimicrobial activity. The comparative embodiment has a 0.3 mm-thick base layer compared with the 0.1 mm-thick base layer of EMBODIMENT 1. The comparative embodiment is also subjected to the antimicrobial activity test by similar testing procedures to those described in the previous embodiment. The antimicrobial activity test results of the comparative embodiment are also recorded on TABLE 3.

TABLE 3

| Mycelial Species | Sort of Glove | Surface of Glove | Time-dependent Variation in Viable Cell Count | |
|---|---|---|---|---|
| | | | Initial Count | After 24 Hrs. |
| *E. coli* | EMBODIMENT 1 | Outer Surface | $1.2 \times 10^5$ | Less Than 10 |
| | | Inner Surface | " | Less Than 10 |
| | COMPARATIVE E | Outer Surface | $1.2 \times 10^5$ | $6.6 \times 10^4$ |
| | | Inner Surface | " | Less Than 10 |
| *S. aureus* | EMBODIMENT 1 | Outer Surface | $1.8 \times 10^5$ | Less Than 10 |
| | | Inner Surface | " | Less Than 10 |
| | COMPARATIVE E | Outer Surface | $1.8 \times 10^5$ | $4.1 \times 10^4$ |
| | | Inner Surface | " | Less Than 10 |

In the embodiments mentioned above, the antimicrobial agent including layer 2 is fabricated on the inner surface 1b of the basic layer 1 of the glove T. On the contrary, even when the antimicrobial agent including layer 2 is fabricated on the outer surface 1a of the basic layer 1 of the glove T, the antimicrobial agent diffusibly moves similarly to EMBODIMENT 1 from the outer surface 1a to the inner surface 1b of the glove T and exhibits the same effectiveness as that of EMBODIMENT 1.

When the inverted glove mentioned above is fabricated by the immersion method which is employed in EMBODIMENT 1, a change in coating sequence can easily give that glove. Namely, the manufacturing mold made of pottery is first immersed in the emulsion composed of the co-polymerized resin of methacrylic acid ester which includes the antimicrobial agent. The mold is subsequently immersed in the polyvinyl chloride paste to form the base layer 1 of the glove thereon. Removing the glove by inverting inside out from the mold can easily give the inverted glove of that of EMBODIMENT 1.

Despite that both inorganic and organic antimicrobial agents can be used as the antimicrobial agent according to the present invention, those having wide antimicrobial spectra such as phosphates-descendent compounds, silicates-descendent compounds and the like which carry metallic ions of silver, copper, zinc etc. or fused salts of metallic oxides are preferably available. One or two sort of the antimicrobial agents listed above is successfully applicable.

Among those antimicrobial agents mentioned above, the zeolite-descendent antimicrobial agents are made by an ion exchange technology wherein ion exchangeable ions existing in a zeolite are either partially or fully ion exchanged with more than one species of ions such as silver, copper, zinc etc. Both natural and synthetic zeolites are employable herein as the zeolite according to the present invention.

The polyvinyl chloride resins used herein in the embodiments are the well-known ones which are composed of the polyvinyl chloride pastes compounded with usually used additives such as the plastilizer, the stabilizer, the thickner etc.

Co-polymers of methacrylic acid esters of which major composition is methyl methacrylate are used as the plastic resin having a high hardness according to the present invention. However, it is not always limited to the materials mentioned above.

As manufacturing methods for manufacturing the polyvinyl chloride resin-made glove, a dip-coating method and a dip-molding method wherein the mold is immersed in the paste sol having fluidity at a room temperature are well-known as well as a spray-coating method. The present invention is applicable not only to all of the methods mentioned above but also to other methods wherein the glove is formed of an extrusion-molded and extruded film by a secondary working procedure. Namely, the technology according to the present invention is applicable to any favorite manufacturing methods to manufacture the polyvinyl chloride resin-made glove.

The glove made of the polyvinyl chloride resin according to the present invention has actual effects as follows:

Namely, the polyvinyl chloride resin-made glove according to the present invention can exterminate not only the bacteria which are dropped on the outer surface and adhered thereon but also the bacteria which are transferred from the fingers and the palm of the hand onto the inner surface of the glove even under the conditions that the bacteria are liable to breed. Accordingly, this glove is most suitable for handling foods, medicines etc.

Moreover, the glove according to the present invention requires only a small amount of the antimicrobial agent addition to obtain a specified antimicrobial activity, which does not hurt the inherent natures of the materials such as the resin etc. to maintain the workability of the resin on the excellent conditions as well as to maintain the economic aspect of the glove at the competitive status.

What is claimed is:

1. A glove comprising:

a base layer formed of a polyvinyl chloride resin; and an antimicrobial agent including layer of which major composition is a polyacrylic resin for including an antimicrobial agent, wherein:

said antimicrobial agent including layer is provided on a member of a group consisting of a front surface and a rear surface of said base layer; and a base layer thickness of said glove is reduced less than 0.2 mm wherethrough said antimicrobial agent can diffusibly transfer from a surface provided with said antimicrobial agent including layer to an opposite surface unprovided with said antimicrobial agent including layer.

2. The glove according to claim 1, wherein:

said antimicrobial agent included in said antimicrobial agent including layer is a member of a group consisting of a synthetic zeolite and a natural zeolite which contains at least one of metallic ions belonging to another group consisting of silver, copper and zinc.

* * * * *